United States Patent
Hoff

(10) Patent No.: US 10,067,210 B2
(45) Date of Patent: Sep. 4, 2018

(54) METHOD AND MAGNETIC RESONANCE APPARATUS FOR RECORDING USAGE DATA FOR LOCAL COILS AND MAGNETIC RESONANCE DEVICE

(71) Applicant: Siemens Aktiengesellschaft, Munich (DE)

(72) Inventor: Maart Hoff, Erlangen (DE)

(73) Assignee: Siemens Aktiengesellschaft, Munich (DE)

(\*) Notice: Subject to any disclaimer, the term of this patent is extended or adjusted under 35 U.S.C. 154(b) by 571 days.

(21) Appl. No.: 14/719,725

(22) Filed: May 22, 2015

(65) Prior Publication Data

US 2015/0338484 A1 Nov. 26, 2015

(30) Foreign Application Priority Data

May 23, 2014 (DE) .................. 10 2014 209 861

(51) Int. Cl.
  *G01R 33/54* (2006.01)
  *G01R 33/341* (2006.01)
  *A61B 5/055* (2006.01)

(52) U.S. Cl.
  CPC ......... *G01R 33/543* (2013.01); *G01R 33/341* (2013.01); *A61B 5/055* (2013.01)

(58) Field of Classification Search
  USPC .................................................. 324/307–316
  See application file for complete search history.

(56) References Cited

U.S. PATENT DOCUMENTS

| | | | |
|---|---|---|---|
| 2006/0232275 A1 | 10/2006 | Leussler | |
| 2007/0103157 A1 | 5/2007 | Campagna | |
| 2010/0156421 A1* | 6/2010 | Sukkau | G01R 33/3415 324/318 |
| 2010/0176800 A1 | 7/2010 | Biber et al. | |
| 2011/0221441 A1 | 9/2011 | Baumgartl et al. | |
| 2013/0181715 A1 | 7/2013 | Biber | |
| 2013/0214784 A1* | 8/2013 | Dietz | G01R 33/3854 324/314 |
| 2013/0293229 A1* | 11/2013 | Lin | G01R 33/483 324/309 |

\* cited by examiner

*Primary Examiner* — Vincent Q Nguyen
(74) *Attorney, Agent, or Firm* — Schiff Hardin LLP

(57) ABSTRACT

In a method and apparatus for recording usage data describing the use of local coils in a magnetic resonance scanner, when a trigger event occurs at least one item of coil information relating to the current configuration of the local coils, and an associated time stamp, are automatically stored as usage data.

12 Claims, 1 Drawing Sheet

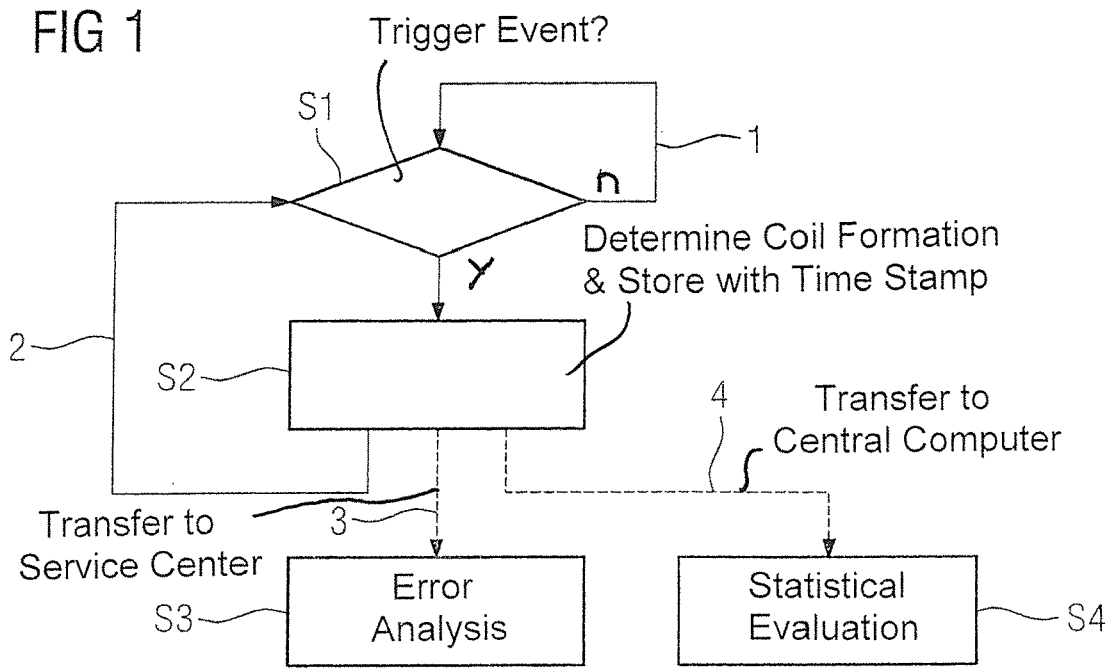
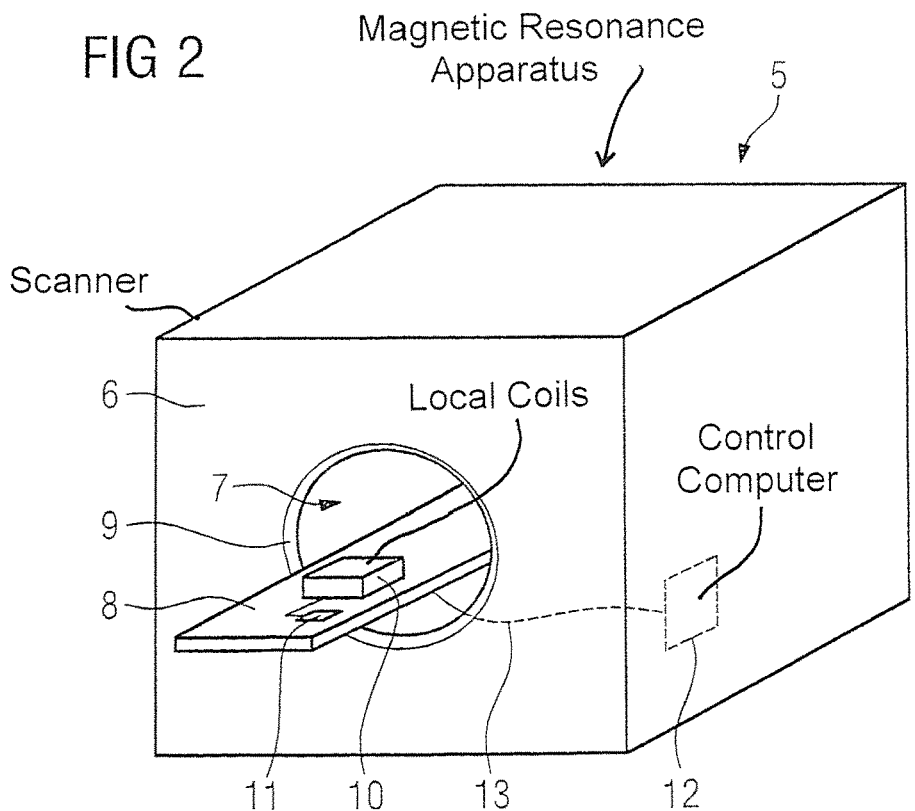

METHOD AND MAGNETIC RESONANCE APPARATUS FOR RECORDING USAGE DATA FOR LOCAL COILS AND MAGNETIC RESONANCE DEVICE

BACKGROUND OF THE INVENTION

Field of the Invention

The present invention concerns a method for recording usage data describing the use of local coils in a magnetic resonance apparatus, as well as a magnetic resonance apparatus that implements such a method.

Description of the Prior Art

Magnetic resonance apparatuses are widely known. They are complex imaging systems, often used for medical purposes. Despite the development effort that has gone into such apparatuses, errors or compromises in the imaging quality can occur. Hence, it is known for protocol files to be created during magnetic resonance measurements (data acquisitions), to help developers to analyze errors, and ideally to suppress them. These protocol files contain, for example, the recording parameters used, in particular the magnetic resonance sequence used, and/or other operating parameters of the magnetic resonance apparatus.

Ever more frequent use is made of local coils in magnetic resonance imaging; in the case of diagnostic measurements such coils are used almost exclusively. These local coils are frequently not permanently connected to the magnetic resonance device, but are retrieved as necessary, placed in the required position and orientation on the patient, and connected by plugs to various slots on the patient bed of the magnetic resonance device. Depending on the local coil configuration that is used, certain modifications of the recording protocols are available or various modifications are executed in the software employed by the magnetic resonance apparatus.

The coil configurations of such local coils are not apparent from the conventional protocol files, and users generally are able to give only insufficient information about the coil configuration. Since problems with the image quality and/or other error states may depend on the local coils used, this makes it much more difficult to search for errors and in some cases even makes finding the error completely impossible. Without information about the coil configuration, it is not possible for all image quality problems to be reliably resolved by users.

At present users have no choice but to manually note the coil configuration and send it to a customer service center. Because of the many details and the frequent lack of time on the part of users, this is frequently not done adequately, making it more difficult to examine errors.

Furthermore, it is not known how users actually use local coils that are sold. This makes it more difficult to plan marketing activities and/or take decisions about the product lifecycle of local coils. Surveying users about coil usage only produces imprecise and inadequate results.

SUMMARY OF THE INVENTION

An object of the invention is to provide a way, requiring little effort, of improving the basis for error analyses and usage statistics of conducted magnetic resonance examinations.

This object is achieved in accordance with the invention by a method for recording usage data describing the use of local coils in a magnetic resonance apparatus, wherein when a trigger event occurs, at least one item of coil information relating to the current configuration of the local coil or coils in use, and an associated time stamp, are automatically stored as usage data.

In accordance with the invention, in addition to the presently documented events and/or parameters, the coil configuration is likewise saved in the protocol files at relevant time points at which a trigger event occurs, in particular in specific files. Thus the coil configuration of the local coils at the magnetic resonance apparatus of the user is saved, which coil configuration has conventionally been unknown or unretrievable. With the inventive method, this knowledge is available in the form of usage data.

The usage data recorded in this way can expediently be employed at a later time in connection with an error analysis and/or a statistical evaluation regarding the use of the local coils, as discussed in detail below. Thus the database for error analyses and statistical evaluations is significantly improved and its quality is significantly increased.

Expediently, the connection and/or removal of a local coil in the magnetic resonance apparatus and/or the selection of a local coil to be used at an operating device of the magnetic resonance apparatus and/or the start of a magnetic resonance measurement with the magnetic resonance apparatus and/or a fault scenario that occurs, can be used as a trigger event. These events represent time points for storing a coil configuration. The start of a measurement is particularly preferred as a trigger event, since the possible errors occur mostly in connection with the measurement, thus the coil configuration at the time of the measurement is a particularly relevant item of information. In many fault scenarios, a provision is already made in the prior art to save log files ("Savelog"). It is expedient to then also store the usage data of the local coils. This avoids local coils not being taken into consideration because of a restricted time coverage due to missing trigger events.

It is furthermore expedient for the type of at least one connected local coil, in particular of all connected local coils, and/or an item of location information of at least one connected local coil, in particular of all local coils, and/or an item of usage information, derived in particular from operator settings, of at least one connected local coil, in particular of all connected local coils, to be used as the at least one item of coil information. Thus in the present method it is possible to document which local coils are present at the current time, which local coils are also in fact used in connection with the measurement, where the various local coils are located, and if necessary other coil information. In this way a precise mapping of the user's coil configuration is obtained.

Most of this information is in principle available in any case. Usage information can be deduced, for example, from operator settings, for example the selection of a local coil at a user interface. The type of the at least one connected local coil can be read from data of an identification device of the local coil, wherein for example different resistance values and/or combinations of resistance values at the slots can be read via corresponding lines. The resistance values are then assigned corresponding coil types, for example whether they are back coils, head coils, etc., and if necessary also other information, for example a type/model of the local coil, etc. Besides the use of resistance values other methods for determining such identification data of the local coils are also known, which of course can likewise be employed.

Regarding the location information, used slot can be used. This already provides approximate information about where and how the local coil is arranged. Preferably however a position and/or orientation in respect of the patient is also used as location information. In this connection, when identification devices based on resistance values are provided, changes can for example be observed in the resistance values when there are changes in the magnetic field, in particular when a gradient is created. These resistance values can contain information about the orientation of the local coil inside the patient aperture of the magnetic resonance device; methods have already been proposed in which at least an approximate determination of the position of the local coil based on resistance values changed by the magnetic field can be communicated by identification devices of the local coil.

Another possibility for determining location information is a simple, short magnetic resonance measurement, from which information about the spatial arrangement of at least one local coil can be obtained. For example, one-dimensional spin echo sequences with a nonselective excitation pulse and rephasing pulse can be used, in which only one readout gradient is active, in order to obtain a one-dimensional projection. In this case two excitations with normal and inverse polarity of the gradient can be recorded, in order to be able to identify local coils situated outside the homogeneity volume. The evaluation is based on complex data which represents the time domain and can be transmitted to the frequency domain by Fourier transformation. The measured spectrum is evaluated by means of suitable algorithms, in order to obtain location information about the local coils in at least one spatial direction. The procedure shown can likewise be regarded as exemplary.

Such methods also thus supply valuable coil information which describes the coil configuration.

The usage data can be stored in a log file (or protocol file). A plurality of embodiments are conceivable here. Initially the log file can be kept at the magnetic resonance apparatus itself, but it is also conceivable for the log file to be provided externally from the magnetic resonance apparatus, by the usage data being transmitted to a computer facility connected via a network. Furthermore, a log file can also relate to a single examination in each case, so that a particularly easy assignment to examinations is possible if an error occurs during an examination and an error analysis needs to be carried out. However, it is also conceivable to use log files that are continued over the longer term, for example to create a new log file whenever a restart is performed.

It is otherwise not absolutely necessary for the usage data for the local coils to be stored in a shared log file with other operating data to be logged for the magnetic resonance device, but it may even be advantageous to use different files here and to provide a log file specifically for the local coils. In particular, it is advantageous for the usage data to be stored in anonymized form in the log file, i.e. independently of patient data, etc., since then the usage data for an error analysis and/or a statistical evaluation can be forwarded without any data protection concerns.

In an embodiment, in a fault scenario, in particular after an input by the operator, the usage data relating to the fault scenario is sent for evaluation to a customer service center, in particular via the internet. A support function may for example be implemented on the magnetic resonance device which enables all data needed for the error analysis, in other words including the usage data, to be sent to a computer facility of a customer service center in the fault scenario by means of a particularly simple operation, where a start can be made on the error analysis immediately. If a statistic evaluation of the usage data is to be carried out, it is of course sufficient to send this for example at pre-set, cyclical points in time or to have this likewise triggered by an operator.

Advantageously, at least one statistical usage variable can be determined in an automatic statistical evaluation from the usage data plotted after several trigger events. Therefore statistics on the local coil usage can be created from the plotted usage data, so that for example it is possible to check which local coils are in fact employed by the users. It is therefore conceivable for the statistical usage variables to describe the usage of individual local coils, in particular the usage frequency. With this information it is for example possible to improve the preparations for marketing campaigns. Rarely used local coils can be discontinued or replaced, including for example in order to reduce the maintenance costs for the local coils.

If the statistical evaluation is to take place with respect to information for manufacturers of the magnetic resonance apparatus or the manufacturer of local coils, it is particularly expedient for usage data for several magnetic resonance apparatuses to be combined for the statistical evaluation. For example, usage data for various magnetic resonance apparatuses can be compiled on a central computer facility, and then evaluated overall, from which for example decisions about the further manufacture or sale of a particular kind of local coil can be derived, etc.

To analyze errors that have occurred, it is particularly expedient for the usage data for a particular configuration to be used in connection with a simulation of a magnetic resonance measurement in a simulation environment. Such an error analysis can be carried out externally of the magnetic resonance apparatus, for example by a manufacturer's customer service center. Since the causes of errors can frequently be traced to the software of the magnetic resonance device, it may be sufficient if the simulation relates to the examination of the functional integrity of said software, so that a simulation of the hardware components is expediently possible. In a simulation environment, in other words simulation software, the user's coil configuration can be reproduced as exactly as possible based on the stored usage data. Moreover it is possible to set and simulate particular coil configurations quickly and with minimal effort for the test during the software development. This makes a realistic test possible and a larger number of scenarios can be covered, since realistic usage data on the local coils is used. If errors are reported, the error can be reproduced and analyzed more quickly and easily because the reproduction of the coil configuration is as exact as possible.

The present invention relates not just to the method, but also to a magnetic resonance apparatus containing a controller configured to implement the inventive method. All embodiments relating to the inventive method can be transferred analogously to the inventive magnetic resonance apparatus, with which the advantages cited can thus likewise be obtained. In particular the controller of the magnetic resonance apparatus can include a trigger unit that monitors the presence of trigger events, wherein on occurrence of the trigger event a storage unit of the controller becomes active and the coil information together with a time stamp is stored as usage data, for example in a log file.

BRIEF DESCRIPTION OF THE DRAWINGS

FIG. 1 is a flowchart of an exemplary embodiment of the inventive method.

FIG. 2 schematically represents an inventive magnetic resonance apparatus.

DESCRIPTION OF THE PREFERRED EMBODIMENTS

FIG. 1 shows a flowchart of an exemplary embodiment of the inventive method. In a step S1 the system is constantly monitored during operation of the magnetic resonance device, as indicated by arrow 1, to see whether trigger events occur which may trigger storage of usage data for the local coils. In this case the connection and removal of a local coil in the magnetic resonance device, the selection of a local coil to be used at an operating device of the magnetic resonance device and the start of a magnetic resonance measurement with the magnetic resonance device are used as trigger events. If a trigger event occurs, a coil formation is determined in step S2 and is stored together with a time stamp as usage data in a log file. In this case a specific log file is used for the local coils, in which only the usage data is held, without any other data, in particular without patient data. New log files can for example be created in each case when the magnetic resonance device is restarted.

The coil information should in this case include the type of all connected local coils, location information for all connected local coils and usage information for all connected local coils derived from operator settings, in order to obtain as exact as possible a map of the coil configuration. The type of a local coil is here determined by reading an identification device of the local coil, wherein, for example, a resistance value can be read by connecting the local coil to a slot of the magnetic resonance device, this resistance value containing information about the local coil connected at this slot. In this respect assignment to the slot which displays first location information is also known. Other location information can likewise be derived from such resistance values, for example the orientation of a local coil, in that the change in the resistance value by the magnetic field prevailing in the magnetic resonance device is evaluated, from which an estimation of the position can be determined. Usage information is normally set by users themselves in connection with measurement planning as part of the recording protocol and for example indicates whether and when a local coil is employed to transmit and/or receive, etc.

After the coil information has been determined in this way, the usage data also containing a time stamp is stored in a log file in step S2. Then as indicated by arrow 2, there is normally a return to step S1 and the system waits for the next trigger event.

However, certain operator actions can, as indicated by the dashed lines 3 and 4, result in evaluations of the usage data which can also be performed on a computer facility external to the magnetic resonance device, for example on a computer facility of a customer service center. Thus when a fault scenario is present, for example when contrary to expectations the image quality is extremely poor, an operator action can be performed to transfer, as represented by dashed line 3, all plotted protocol data, in other words including the usage data, to a computer facility of the customer service center, where an error analysis is performed in step S3. To this end it can be provided for the usage data to be employed in a simulation environment in order to reproduce the coil configuration as exactly as possible.

Another possibility for the further evaluation relates is to make a statistical evaluation of the usage data in step S4, in particular as to how frequently particular local coils are employed. This can be described by a statistical usage variable. Precisely when cross-device conclusions are to be drawn, it is expedient if the statistical evaluation in step S4 takes place on a central computer facility which combines the usage data from several magnetic resonance devices. Such an operator-performed transfer to a central computer is represented by dashed line 4. Decisions can then for example be taken for marketing campaigns and/or it is possible to decide about the continuation or further development of certain types of local coils.

FIG. 2 shows a highly simplified schematic diagram of an inventive magnetic resonance apparatus 5. As is known in principle, this has a main magnet unit 6 (scanner) which defines a patient aperture 7, into which a patient can be transported by means of a patient bed 8. Surrounding the patient aperture 7 is a module 9 containing a gradient coil arrangement and a radio-frequency coil arrangement of the scanner.

The magnetic resonance apparatus 5 have one or more of local coils 10, which can be suitably arranged on a patient (not shown in detail) positioned on the patient bed 8, and can be connected via slots 11 in or on the patient couch 8. Although in this case only one local coil 10 and one slot 11 is shown. The number of slots 11 is normally larger and of course more than one local coil 10 can be used.

The operation of the magnetic resonance device 5 is controlled by a control computer 12 which, indicated here only schematically by the connection 13, can also communicate with the slots 11 on or at the patient couch 8. Thus for example coil information can be retrieved from identification devices of the local coils 10.

The control computer 12 is designed to perform the inventive method, and consequently has a trigger unit that monitors the occurrence of trigger events, and a storage unit that determines the coil information as per step S2 and stores it together with a time stamp as usage data in a log file on a storage device of the control computer 12.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for recording usage data describing use of a local radio frequency (RF) coil in a magnetic resonance apparatus, comprising:

operating a magnetic resonance apparatus in a current procedure comprising use of at least one local RF coil to acquire magnetic resonance data from a subject situated in the magnetic resonance apparatus, said local RF coil being selectively configurable in respectively different configurations in different procedures, and having a current configuration in said current procedure;

in a control computer that operates said magnetic resonance apparatus to execute said current procedure, designating a trigger event that occurs during said current procedure; and detecting occurrence of said trigger event and, upon detection of the occurrence of said trigger event, automatically recording, in said control computer, at least one item of coil information that describes said current configuration of the local RF coil as used in said current procedure, associating a time stamp with said coil information, and storing the coil information with the associated time stamp as usage data for said local RF coil.

2. A method as claimed in claim 1 comprising selecting said trigger event from the group consisting of electrical connection of said local RF coil in said magnetic resonance apparatus, electrical disconnection of said local RF coil in said magnetic resonance apparatus, selection of said local RF coil for use in said procedure, starting said current procedure, and occurrence of a fault scenario in said current procedure.

3. A method as claimed in claim 1 comprising selecting said item of information from the group consisting of a type of said local RF coil, location of said local RF coil in said magnetic resonance apparatus during said current procedure, and operator settings affecting said local RF coil in said current procedure.

4. A method as claimed in claim 3 wherein said item of coil information is a type of said local RF coil, and comprising reading said type from data embodied in an identification device of said local RF coil.

5. A method as claimed in claim 3 wherein said item of coil information is a position or orientation of said local RF coil in said magnetic resonance apparatus, and wherein said local RF coil is electrically connected to one of a plurality of available sockets on a patient bed of the magnetic resonance apparatus, and wherein the socket to which the local RF coil is connected serves as an indicator of said position or orientation, and comprising detecting the socket to which the local RF coil is connected in order to determine said item of coil information.

6. A method as claimed in claim 1 comprising storing said usage data as a log file.

7. A method as claimed in claim 1 wherein said trigger event is a fault scenario and comprising, upon detection of the occurrence of said fault scenario, automatically transmitting said usage data, including a description of said fault scenario, to a customer service center that is remote from said processor and, at said customer service center, automatically analyzing said usage data.

8. A method as claimed in claim 1 comprising, after executing a plurality of procedures, respectively at different times, using said local RF coil, each procedure, at the time it is executed, serving as said current procedure, statistically analyzing said usage data for the plurality of procedures, and producing at least one statistical usage variable from said statistical analysis of said usage data for the plurality of procedures.

9. A method as claimed in claim 7 comprising executing said statistical analysis of said usage data for the plurality of procedures to produce said statistical usage variable as an indicator of a usage frequency of said local RF coil.

10. A method as claimed in claim 7 comprising compiling said usage data from said plurality of procedures implemented in a plurality of magnetic resonance apparatuses.

11. A method as claimed in claim 1 comprising executing a computerized simulation of a magnetic resonance data acquisition using said usage data as an input to said simulation.

12. A magnetic resonance apparatus comprising:
a magnetic resonance scanner comprising at least one local RF coil to be used in a current procedure, said local RF coil being selectively configurable in respectively different configurations in different procedures, and having a current configuration in said current procedure;
a control computer configured to operate said magnetic resonance scanner to execute said current procedure in which said local RF coil is used, and said control computer being configured to detect a trigger event that occurs during said current procedure;
an electronic memory in, or in communication with, said control computer; and
said control computer being configured, upon detecting said trigger event, to obtain at least one item of coil information describing said current configuration of said at least one local RF coil in said current procedure, and to associate a time stamp with said at least one item of coil information, and to store said at least one item of coil information and the associated time stamp as usage data in said electronic memory, thereby producing a data file of said usage data for said local RF coil.

* * * * *